(12) United States Patent
Economides et al.

(10) Patent No.: US 7,285,532 B2
(45) Date of Patent: Oct. 23, 2007

(54) THERAPEUTIC METHOD FOR TREATING BONE FORMATION DISEASES

(75) Inventors: Aris N. Economides, Tarrytown, NY (US); Neil Stahl, Carmel, NY (US); David M. Valenzuela, Yorktown Heights, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 536 days.

(21) Appl. No.: 10/735,345

(22) Filed: Dec. 12, 2003

(65) Prior Publication Data

US 2004/0132661 A1 Jul. 8, 2004

Related U.S. Application Data

(63) Continuation-in-part of application No. 09/897,322, filed on Jul. 2, 2001, now abandoned, which is a continuation of application No. 08/392,935, filed as application No. PCT/US93/08326 on Sep. 2, 1993, now Pat. No. 5,843,775, which is a continuation-in-part of application No. 07/957,401, filed on Oct. 6, 1992, now abandoned, which is a continuation-in-part of application No. 07/950,410, filed on Sep. 23, 1992, now abandoned, which is a continuation-in-part of application No. 07/939,954, filed on Sep. 3, 1992, now abandoned.

(51) Int. Cl.
*A61K 38/16* (2006.01)

(52) U.S. Cl. .................. 514/12; 514/2; 514/8

(58) Field of Classification Search ............ None
See application file for complete search history.

(56) References Cited

U.S. PATENT DOCUMENTS 4,857,637 A 8/1989 Hammonds et al.
4,933,294 A 6/1990 Waterfield et al.
5,030,576 A 7/1991 Dull et al.

FOREIGN PATENT DOCUMENTS

WO WO 92/00524 4/1992

OTHER PUBLICATIONS

Yanagita, 2005, Cytokine and Growth Factor Reviews 16:309-317.*
Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Zimmerman et al., 1996, Cell 86:599-606.*
Hanallah et al., 2004, J. Bone Joint Surg. 86 :80-91.*
Glaser et al., 2003, J. Bone Joint Surg. 85 :2332-2342.*
Waite et al., 2003, Nature Reviews Genetics 4(10):763-773.*
DEVELOPMENT, vol. 111, issued 1991, Christian, J., et al., "Xwnt-8, a Xenopus Wnt-1/int-1 related gene responsive to mesoderm-inducing growth factors, may play a role in ventral mesodermal patterning during embryogenesis," pp. 1045-1055.
NATURE, vol. 361, issued Feb. 11, 1993, Smith, W.C., et al., "Secreted noggin protein mimics the Spemann organizer in dorsalizing *Xenopus mesoderm*," pp. 547-549.
CELL, vol. 67, issued Nov. 15, 1991, Smith, W.C., and Harland, R.M., "Injected Xwnt-8 RNA Acts Early in Xenopus Embryos to Promote Formation of a Vegetal Dorsalizing Center", pp. 753-765.
Brunet et al., Science, vol. 280, pp. 1455-1457, 1998.
Jackowski, A., British J. of Neurosurgery, vol. 9, pp. 303-317, 1995.
Pepeu, G., et al., Drug Design and Delivery, vol. 7, pp. 1-10, 1990.

* cited by examiner

*Primary Examiner*—Elizabeth C. Kemmerer
(74) *Attorney, Agent, or Firm*—Valeta Gregg, Esq.; Tor E. Smeland, Esq.

(57) ABSTRACT

Methods of treating and/or inhibiting a bone morphogenetic protein (BMP)-related disorder or condition by administering a BMP antagonist to a subject suffering from a BMP-related disorder or condition such that the BMP-related disorder or condition is treated. The method is carried out with a human noggin or a human noggin deletion mutant.

4 Claims, No Drawings

SEQUENCE LISTING

<160> NUMBER OF SEQ ID NOS: 10

<210> SEQ ID NO 1
<211> LENGTH: 699
<212> TYPE: DNA
<213> ORGANISM: Homo sapien
<220> FEATURE:
<221> NAME/KEY: CDS
<222> LOCATION: (1)...(699)

<400> SEQUENCE: 1

```
atg gag cgc tgc ccc agc cta ggg gtc acc ctc tac gcc ctg gtg gtg      48
Met Glu Arg Cys Pro Ser Leu Gly Val Thr Leu Tyr Ala Leu Val Val
 1               5                  10                  15 gtc ctg ggg ctg cgg gcg aca ccg gcc ggc ggc cag cac tat ctc cac      96
Val Leu Gly Leu Arg Ala Thr Pro Ala Gly Gly Gln His Tyr Leu His
                20                  25                  30 atc cgc ccg gca ccc agc gac aac ctg ccc ctg gtg gac ctc atc gaa     144
Ile Arg Pro Ala Pro Ser Asp Asn Leu Pro Leu Val Asp Leu Ile Glu
            35                  40                  45 cac cca gac cct atc ttt gac ccc aag gaa aag gat ctg aac gag acg     192
His Pro Asp Pro Ile Phe Asp Pro Lys Glu Lys Asp Leu Asn Glu Thr
        50                  55                  60 ctg ctg cgc tcg ctg ctc ggg ggc cac tac gac cca ggc ttc atg gcc     240
Leu Leu Arg Ser Leu Leu Gly Gly His Tyr Asp Pro Gly Phe Met Ala
65                  70                  75                  80 acc tcg ccc ccc gag gac cgg ccc ggc ggg ggc ggt gca gct ggg         288
Thr Ser Pro Pro Glu Asp Arg Pro Gly Gly Gly Gly Ala Ala Gly
                85                  90                  95 ggc gcg gag gac ctg gcg gag ctg gac cag ctg ctg cgg cag cgg ccg     336
Gly Ala Glu Asp Leu Ala Glu Leu Asp Gln Leu Leu Arg Gln Arg Pro
            100                 105                 110 tcg ggg gcc atg ccg agc gag atc aaa ggg cta gag ttc tcc gag ggc     384
Ser Gly Ala Met Pro Ser Glu Ile Lys Gly Leu Glu Phe Ser Glu Gly
        115                 120                 125 ttg gcc cag ggc aag aag cag cgc cta agc aag aag ctg cgg agg aag     432
Leu Ala Gln Gly Lys Lys Gln Arg Leu Ser Lys Lys Leu Arg Arg Lys
    130                 135                 140 tta cag atg tgg ctg tgg tcg cag aca ttc tgc ccc gtg ctg tac gcg     480
Leu Gln Met Trp Leu Trp Ser Gln Thr Phe Cys Pro Val Leu Tyr Ala
145                 150                 155                 160 tgg aac gac ctg ggc agc cgc ttt tgg ccg cgc tac gtg aag gtg ggc     528
Trp Asn Asp Leu Gly Ser Arg Phe Trp Pro Arg Tyr Val Lys Val Gly
                165                 170                 175 agc tgc ttc agt aag cgc tcg tgc tcc gtg ccc gag ggc atg gtg tgc     576
Ser Cys Phe Ser Lys Arg Ser Cys Ser Val Pro Glu Gly Met Val Cys
            180                 185                 190 aag ccg tcc aag tcc gtg cac ctc acg gtg ctg cgg tgg cgc tgt cag     624
Lys Pro Ser Lys Ser Val His Leu Thr Val Leu Arg Trp Arg Cys Gln
```

```
                 195                 200                 205
cgg cgc ggg ggc cag cgc tgc ggc tgg att ccc atc cag tac ccc atc      672
Arg Arg Gly Gly Gln Arg Cys Gly Trp Ile Pro Ile Gln Tyr Pro Ile
    210                 215                 220 att tcc gag tgc aag tgc tcg tgc tag                                  699
Ile Ser Glu Cys Lys Cys Ser Cys  *
225                 230
```

<210> SEQ ID NO 2
<211> LENGTH: 232
<212> TYPE: PRT
<213> ORGANISM: Homo sapien

<400> SEQUENCE: 2

```
Met Glu Arg Cys Pro Ser Leu Gly Val Thr Leu Tyr Ala Leu Val Val
1               5                   10                  15

Val Leu Gly Leu Arg Ala Thr Pro Ala Gly Gly Gln His Tyr Leu His
            20                  25                  30

Ile Arg Pro Ala Pro Ser Asp Asn Leu Pro Leu Val Asp Leu Ile Glu
        35                  40                  45

His Pro Asp Pro Ile Phe Asp Pro Lys Glu Lys Asp Leu Asn Glu Thr
    50                  55                  60

Leu Leu Arg Ser Leu Leu Gly Gly His Tyr Asp Pro Gly Phe Met Ala
65                  70                  75                  80

Thr Ser Pro Pro Glu Asp Arg Pro Gly Gly Gly Gly Ala Ala Gly
                85                  90                  95

Gly Ala Glu Asp Leu Ala Glu Leu Asp Gln Leu Leu Arg Gln Arg Pro
                100                 105                 110

Ser Gly Ala Met Pro Ser Glu Ile Lys Gly Leu Glu Phe Ser Glu Gly
            115                 120                 125

Leu Ala Gln Gly Lys Lys Gln Arg Leu Ser Lys Lys Leu Arg Arg Lys
130                 135                 140

Leu Gln Met Trp Leu Trp Ser Gln Thr Phe Cys Pro Val Leu Tyr Ala
145                 150                 155                 160

Trp Asn Asp Leu Gly Ser Arg Phe Trp Pro Arg Tyr Val Lys Val Gly
                165                 170                 175

Ser Cys Phe Ser Lys Arg Ser Cys Ser Val Pro Glu Gly Met Val Cys
            180                 185                 190

Lys Pro Ser Lys Ser Val His Leu Thr Val Leu Arg Trp Arg Cys Gln
        195                 200                 205

Arg Arg Gly Gly Gln Arg Cys Gly Trp Ile Pro Ile Gln Tyr Pro Ile
    210                 215                 220

Ile Ser Glu Cys Lys Cys Ser Cys
225                 230
```

<210> SEQ ID NO 3
<211> LENGTH: 36
<212> TYPE: DNA
<213> ORGANISM: Artificial Sequence
<220> FEATURE:
<223> OTHER INFORMATION: Oligonucleotide

<400> SEQUENCE: 3

```
gactcgagtc gacatcgcag atgtggctgt ggtcac                               36
```

<210> SEQ ID NO 4
<211> LENGTH: 37
<212> TYPE: DNA

```
<213> ORGANISM: Artificial Sequence
<220> FEATURE:
<223> OTHER INFORMATION: Oligonucleotide

<400> SEQUENCE: 4
ccaagcttct agaattcgca ggaacactta cactcgg                          37

<210> SEQ ID NO 5
<211> LENGTH: 18
<212> TYPE: DNA
<213> ORGANISM: Artificial Sequence
<220> FEATURE:
<223> OTHER INFORMATION: Oligonucleotide

<400> SEQUENCE: 5
cagatgtggc tgtggtca                                              18

<210> SEQ ID NO 6
<211> LENGTH: 6
<212> TYPE: PRT
<213> ORGANISM: Mus Musculus

<400> SEQUENCE: 6

Gln Met Trp Leu Trp Ser
 1               5

<210> SEQ ID NO 7
<211> LENGTH: 18
<212> TYPE: DNA
<213> ORGANISM: Artificial Sequence
<220> FEATURE:
<223> OTHER INFORMATION: Oligonucleotide

<400> SEQUENCE: 7
gcaggaacac ttacactc                                              18

<210> SEQ ID NO 8
<211> LENGTH: 6
<212> TYPE: PRT
<213> ORGANISM: Mus musculus

<400> SEQUENCE: 8

Glu Cys Lys Cys Ser Cys
 1               5

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: 3, 18
<223> OTHER INFORMATION: R = A or G
<220> FEATURE:
<221> NAME/KEY: modified_base
<222> LOCATION: 6, 12
<223> OTHER INFORMATION: N = i - inosine
<220> FEATURE:
<221> NAME/KEY: modified_base
<222> LOCATION: 15
<223> OTHER INFORMATION: Y = C or T

<400> SEQUENCE: 9
garggnatgg tntgyaarcc                                            20
```

-continued

```
<210> SEQ ID NO 10
<211> LENGTH: 220
<212> TYPE: PRT
<213> ORGANISM: Artificial Sequence
<220> FEATURE:
<223> OTHER INFORMATION: noggin deletion mutein

<400> SEQUENCE: 10

Met Glu Arg Cys Pro Ser Leu Gly Val Thr Leu Tyr Ala Leu Val Val
1               5                   10                  15

Val Leu Gly Leu Arg Ala Thr Pro Ala Gly Gly Gln His Tyr Leu His
            20                  25                  30

Ile Arg Pro Ala Pro Ser Asp Asn Leu Pro Leu Val Asp Leu Ile Glu
        35                  40                  45

His Pro Asp Pro Ile Phe Asp Pro Lys Glu Lys Asp Leu Asn Glu Thr
    50                  55                  60

Leu Leu Arg Ser Leu Leu Gly Gly His Tyr Asp Pro Gly Phe Met Ala
65                  70                  75                  80

Thr Ser Pro Pro Glu Asp Arg Pro Gly Gly Gly Gly Ala Ala Gly
                85                  90                  95

Gly Ala Glu Asp Leu Ala Glu Leu Asp Gln Leu Leu Arg Gln Arg Pro
            100                 105                 110

Ser Gly Ala Met Pro Ser Glu Ile Lys Gly Leu Glu Phe Ser Glu Gly
            115                 120                 125

Leu Ala Gln Gly Leu Gln Met Trp Leu Trp Ser Gln Thr Phe Cys Pro
    130                 135                 140

Val Leu Tyr Ala Trp Asn Asp Leu Gly Ser Arg Phe Trp Pro Arg Tyr
145                 150                 155                 160

Val Lys Val Gly Ser Cys Phe Ser Lys Arg Ser Cys Ser Val Pro Glu
                165                 170                 175

Gly Met Val Cys Lys Pro Ser Lys Ser Val His Leu Thr Val Leu Arg
            180                 185                 190

Trp Arg Cys Gln Arg Arg Gly Gly Gln Arg Cys Gly Trp Ile Pro Ile
        195                 200                 205

Gln Tyr Pro Ile Ile Ser Glu Cys Lys Cys Ser Cys
    210                 215                 220
```

THERAPEUTIC METHOD FOR TREATING BONE FORMATION DISEASES

CROSS-REFERENCE TO RELATED APPLICATIONS

This application is a continuation-in-part of U.S. Ser. No. 09/897,322 filed 2 Jul. 2001, which is a continuation of U.S. Ser. No. 08/392,935 filed 22 Sep. 1995, which is a national stage of PCT/US93/08326 filed 2 Sep. 1993, which is a continuation-in-part of U.S. Ser. No. 07/957,401, now abandoned, filed 6 Oct. 1992, which is a continuation-in-part of U.S. Ser. No. 07/950,410, now abandoned, filed on 23 Sep. 1992, which is a continuation-in-part of U.S. Ser. No. 07/939,954, now abandoned, filed 3 Sep. 1992.

STATEMENT REGARDING FEDERALLY SPONSORED RESEARCH

This invention was made, in part, with government support under Grant Contract No. ROI-GM-42341, awarded by the National Institutes of Health. The government has certain rights in this invention.

REFERENCE TO SEQUENCE LISTING

This disclosure refers to and includes amino acid and nucleic acid sequences, which sequences are referred to by sequence identifiers and included in the Sequence Listing appended to the specification.

FIELD OF THE INVENTION

The invention generally relates to antagonists of bone morphogenetic proteins (BMPs), and more specifically to the use of a BMP antagonist, noggin, for modulation of heterotopic ossification bone growth, hair growth, and other BMP-driven biological processes in humans.

STATEMENT OF RELATED ART

Noggin is a bone morphogenetic protein (BMP) known to bind BMP2, BMP4, BMP5, BMP6, BMP7 and related proteins GDF5, GDF6, and GDF7 (see, for example, Brunet et al. (1998) Science 280:1455-1457).

BRIEF SUMMARY OF THE INVENTION

This invention is based in part on the discovery that noggin, a secreted polypeptide that functions as a high-affinity antagonists of several members of the bone morphogenetic protein family (BMPs, GDFs, and related proteins), functions in a mouse model of human bone formation disease to block BMP-induced heterotopic ossification.

Accordingly, in one aspect, the invention features a method of treating and/or inhibiting the progression of a bone morphogenetic protein (BMP)-related disorder or condition, comprising administering a BMP antagonist to a subject suffering from a BMP-related disorder or condition, wherein the BMP-related disorder or condition is treated.

In one embodiment, a BMP-related condition or disorder is one in which a BMP antagonist is lacking. In another embodiment, the condition is one in which administration of a BMP antagonist leads to a desirable outcome in a clinical, but not necessarily pathological, situation, e.g., for example, hair loss. In a more specific embodiment, the BMP-related disorder or condition is heterotopic cranial synostosis (HO), fibrodysplasia ossificans progressiva (FOP), or sclerostosis.

In one embodiment, the BMP antagonist is a protein or a nucleic acid molecule encoding a BMP antagonist. In a more specific embodiment, the BMP antagonist is human noggin (hNOG) (SEQ ID NO:2), or a fragment thereof capable of acting as a BMP antagonist. In another specific embodiment, the BMP-4 antagonist is a mutant or variant of human noggin capable of blocking BMP. Still more specifically, the mutant or variant of hNOG is a deletion mutein, wherein the heparin-binding site of hNOG is removed, for example, hNOGΔB2 (SEQ ID NO:10). In another embodiment, the nucleic acid molecule encodes noggin or a noggin mutein.

In a second aspect, the invention features a method of blocking biological activity of a bone morphogenetic protein (BMP) in a subject, comprising administering an agent capable of blocking BMP biological activity.

Other objects and advantages will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe the methods and/or materials in connection with which the publications are cited.

General Description

The cDNA for human noggin (hNOG) (SEQ ID NO:1) was cloned and found to contain a single reading frame encoding a 26 kDa protein (SEQ ID NO:2) with a hydrophobic amino-terminal sequence. Noggin is secreted in vivo as a dimeric glycoprotein with a starting apparent molecular weight of about 33 kDa (as the wild-type subunit). When not glycosylated, the monomeric unit has an apparent molecular weight as measured by SDS-PAGE of about 25-30 kDa.

Nucleic Acid Constructs and Expression

The present invention provides for nucleic acid molecules encoding human noggin (hNOG), and variants, mutants, and fragments thereof capable of acting as antagonists to BMPs. The nucleic acid molecules of the invention may encode naturally occurring hNOG and fragments thereof, or functionally equivalent variants of the naturally-occurring (wild-type) human protein. Amino acid sequence variants of each receptor component may also be prepared by creating mutations in the encoding nucleic acid molecules. Such variants include, for example, deletions from, or insertions or substitutions of, amino acid residues within the amino acid sequence of hNOG. Any combination of deletion, insertion, and substitution may be made to arrive at a final construct, provided that the final construct possesses the ability to block a BMP.

These nucleic acid molecules are inserted into a vector that is able to express the fusion proteins when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion proteins of the invention under control of transcriptional/translational control signals.

Expression of the nucleic acid molecules of the invention may be regulated by a second nucleic acid sequence so that the molecule is expressed in a host transformed with the recombinant DNA molecule. For example, expression may be controlled by any promoter/enhancer element known in the art. Promoters which may be used to control expression of the chimeric polypeptide molecules include, but are not limited to, a long terminal repeat (Squinto et al. (1991) Cell 65:1-20); SV40 early promoter region, CMV, M-MuLV, thymidine kinase promoter, the regulatory sequences of the metallothionine gene; prokaryotic expression vectors such as the b-lactamase promoter, or the tac promoter (see also "Useful proteins from recombinant bacteria" in Scientific American (1980) 242:74-94); promoter elements from yeast or other fungi such as the Gal 4 promoter, ADH, PGK, alkaline phosphatase, and tissue-specific transcriptional control regions derived from genes such as elastase I.

Methods of Administration

The invention provides methods of treatment comprising administering to a subject an effective amount of a BMP antagonist of the invention. In a preferred aspect, the BMP antagonist is substantially purified (e.g., substantially free from substances that limit its effect or produce undesired side-effects). The subject is preferably a mammal, and most preferably a human.

Various delivery systems are known and can be used to administer an agent of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, intraocular, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g. daily, weekly, monthly, etc.) or in combination with other agents. Pulmonary administration can also be employed, e.g., by use of an inhaler or nebulizer, and formulation with an aerosolizing agent.

In another embodiment, the active agent can be delivered in a vesicle, in particular a liposome, in a controlled release system, or in a pump. In another embodiment, polymeric materials can be used (see Howard et al. (1989) J. Neurosurg. 71:105). In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), by direct injection, or by use of microparticle bombardment, or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

Pharmaceutical Compositions

The present invention also provides pharmaceutical compositions comprising a BMP antagonist of the invention. Such compositions comprise a therapeutically effective amount of one or more traps, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin.

The BMP antagonists of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the BMP antagonist that will be effective for its intended therapeutic use can be determined by standard clinical techniques based on the present description. In addition, in vitro assays may optionally be employed to help identify optimal dosage ranges. Generally, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Cellular Transfection and Gene Therapy

The present invention encompasses the use of nucleic acids encoding a BMP antagonist of the invention for transfection of cells in vitro and in vivo. These nucleic acids can be inserted into any of a number of well-known vectors for transfection of target cells and organisms. The nucleic acids are transfected into cells ex vivo and in vivo, through the interaction of the vector and the target cell. The compositions are administered (e.g., by injection into a muscle) to a subject in an amount sufficient to elicit a therapeutic response. An amount adequate to accomplish this is defined as "a therapeutically effective dose or amount."

In another aspect, the invention provides a method of reducing BMP levels in a human or other animal comprising transfecting a cell with a nucleic acid encoding a fusion polypeptide of the invention, wherein the nucleic acid comprises an inducible promoter operably linked to the nucleic acid encoding the BMP antagonist of the invention. For gene therapy procedures in the treatment or prevention of human disease, see for example, Van Brunt (1998) Biotechnology 6:1149-1154.

Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Specific Embodiments

A percutaneous bone induction model of BMP-induced osteogenesis was used to evaluate the effectiveness of noggin as a potential inhibitor of heterotopic ossification. As described below, rhBMP4 protein or buffer was combined with Matrigel™ carrier and the mixture was injected subcutaneously into mice. The ability of rhBMP4-impregnated carrier to induce heterotopic ossification was determined by histological examination of the implants as described in methods. This model reproduced the characteristic stages of rhBMP-induced endochondral bone formation and mimics all the stages of heterotopic ossification seen during ectopic bone induction in FOP. FOP lesions are staged histologically based on the pathologic and morphologic characteristic and have been designated 1A, 1B, 1C, 2A, 2B, and 2C (Gannon et al. (1998) Clin. Orthop. 346:19-25; Gannon et al. (2001) Hum. Pathol. 32(8):84208). 1A lesions are characterized by an intense perivascular lymphocytic aggregation without invasion into the surrounding tissues. 1B lesions involve lymphocytic infiltration from the vessels into the surrounding muscle with myocytolysis and myonecrosis. 1C lesions are characterized by the appearance of fibroproliferative tissue that surrounds and invades the adjacent muscle. As the lesion progresses, a pronounced vascularity is noticed (stage 2A). Stage 2B is identified by the appearance of cartilage. The final stage (2C) is characterized by the appearance of endochondral bone formation with mature heterotopic bone.

In the percutaneous bone induction model, endochondral ossification occurred in a reproducible and dose-dependent cascade following rhBMP4 implantation. At 40 hours following implantation, a pronounced inflammatory response was noted at the implant margins in the presence of rhBMP4. This inflammatory response increased over 56 hours, with a transition zone of mixed inflammatory cells and small capillaries between the implant and skeletal muscle, similar to findings seen in stages 1A and 1B of an FOP lesion. The inflammatory phase was followed by an angiogenic, fibroproliferative stage (72 hours) which surrounded the implant and showed peripheral invasion of the implant, as seen in stage 1C of an FOP lesion. Between 5 and 7 days, a fibroproliferative lesion replaced the periphery of the implant and created deep vascular septations in the implants mimicking the fibroproliferation seen in FOP at stage 2A. By 7 days, mesenchymal cell condensations containing chondrocytes were observed, as in FOP stage 2B. The cartilage matrix became mineralized by 10 days, and mature heterotopic bone with the appearance of marrow elements was present by 14 days, as in FOP stage 2C.

When carrier was injected without the addition of BMP4, a minimal inflammatory response was noted at 24 hours after implantation and was accompanied by a thin fibroproliferative layer that encapsulated the implant after two weeks. Systemic administration of hNOG (100 µg intraperitoneally, every other day for 14 days) was not effective in preventing rhBMP4-induced heterotopic ossification, consistent with data showing that hNOG displays a very short half-life and poor bioavailability. Local administration of hNOG (equimolar amounts of hNOG and rhBMP2 combined with the carrier) was effective in inhibiting heterotopic ossification (data not shown). Therefore, these results indicate that hNOG can be used to block rhBMP2-mediated bone formation by local administration in vivo, but not by systemic administration, in agreement with previous data demonstrating that local delivery of noggin inhibits intramembranous ossification (Aspenberg et al. (2001) J. Bone Miner. Res. 16(3):497-500).

Human noggin (hNOG) contains a heparin-binding domain that confers a high binding affinity to heparin proteoglycans in the extracellular matrix. hNOG injected intravenously into rats or mice displays poor bioavailability and a half-life of less than 30 minutes. We hypothesized that removal of the heparin-binding domain would result in a noggin form that circulates systemically and displays a longer half-life than hNOG. A human noggin mutein, hNOGΔB2 (SEQ ID NO:10), with a deletion between amino acids 133 and 144 that removes the heparin binding domain was generated. Compared to wild-type noggin, hNOGΔB2 displays dramatically reduced binding to heparan sulphate proteoglycans and has only slightly reduced ability for blocking rhBMP4.

In vivo, hNOGΔB2 displays a longer half-life and improved bioavailability upon systemic administration compared to hNOG. Intraperitoneal injections of 250 µg of hNOG into adult BALB/c mice failed to yield any detectable hNOG in animal sera at 30 minutes, 2 hours, or 6 hours post-administration. In contrast, hNOGΔB2 was detected at levels ranging between 0.5 and 1.4 µg/ml 2 hours following injection and remaining at 0.2 to 0.8 µg/ml at 6 hours.

An adenovirus-mediated gene transfer of hNOGΔB2 was used to develop a gene therapy approach for the prevention of BMP-induced heterotopic ossification. Adenoviruses encoding hNOGΔB2 (H5.010CMVhNOGΔB2) or LacZ (H5.010CMVLacZ) were produced and delivered by tail vein injection at various titer doses as described in Methods. Four days after viral injection, mice were implanted percutaneously with Matrigel impregnated with either buffer or rhBMP4. Matrigel implants were recovered at 7 and 14 days post-implantation for histological examination and assessment of bone formation. The implants containing rhBMP4 implanted in animals that were pretreated with low viral titer ($1\times10^{10}$ particles/ml) of either H5.010CMVhNOGΔB2 or with H5.010CMVLacZ induced an aggressive, fibroproliferative lesion with early cartilage formation at 7 days, and heterotopic ossification at 14 days. However, in animals treated with high titer ($1\times10^{11}$) H5.010CMVhNOGΔB2, the implants with rhBMP4 demonstrated a minimal, mixed inflammatory cell infiltrate at 7 days and a thin pseudocapsule several cell layers thick surrounding the unresorbed Matrigel plug at 14 days indistinguishable from carrier implants with no BMP.

Noggin serum levels were measured using a two-site ELISA for noggin. Sera from mice treated with high titer of H5.010CMVhNOGΔB2 contained an average of 121 μg/ml of hNOGΔB2 at four days after delivery of the virus and remained detectable at 18 days. In contrast, mice injected with low titer of H5.010CMVhNOGΔB2 and in which rhBMP4-induced bone formation was not blocked, contained no detectable levels of hNOGΔB2 in their sera.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric. Production of Xenopus embryos is described in U.S. Pat. No. 6,277,593, and Smith & Harlan (1991) Cell 67:753-765, both of which publications are specifically incorporated by reference in their entirety.

Example 1

Cloning of the Human Noggin Homolog

Two oligonucleotides were synthesized based on the mouse noggin sequence: noggin 5' (SEQ ID NO:5) corresponding to amino acids SEQ ID NO:6, and noggin 3' (SEQ ID NO:7) corresponding to SEQ ID NO:8.

The oligonucleotides were used for PCR amplification of a segment of DNA of 260 nucleotides using as a template a mouse cDNA clone prepared as set forth in Example 3 of U.S. Pat. No. 6,277,593. The amplified fragment had a nucleotide sequence that corresponds to nucleotides 2 through 262 of the partial mouse noggin sequence. After amplification, the PCR reaction was electrophosed in agarose gels, the DNA band of 260 nts purified by Magic PCR (Promega), and used as template for the probe labeling reaction. The probe was labeled using a standard PCR reaction (Perkin-Elmer) on 20 ng of DNA template and 0.2 m Curie of alpha $^{32}$P-dCTP (Du Pont 3000 Ci/mmol) instead of dCTP. Unincorporated label was separated from the probes on a G50 NICK column (Pharmacia). The excluded volume of the reaction contained a total of $1.8\times10^8$ cpm. In addition, one degenerated oligonucleotide, named noggin D, corresponding to conserved mouse and Xenopus noggin sequences, was synthesized as follows: Noggin D (SEQ ID NO:9) was labeled by kinase reaction using T4 polynucleotide kinase and gamma $^{32}$P-ATP. The labeled oligonucleotide was purified by NAP5 (Pharmacia) column and used for library hybridization.

Library Screen. A human placental genomic library (Clontech Cat#HL1067J, average insert size 15 kb) in vector EMBL-3 was plated according to manufacturer specifications in NM 538 *E. coli*. Approximately 3 million plaques were transferred to nitrocellulose filters (BA-85 Schleicher and Schuell) in three replicas (named A, B and C) and screened according to Maniatis, et al. (Sambrook, et al. (1989) Molecular cloning a laboratory manual, CSH Lab Press, New York). The replica filters A and C were hybridized in a buffer containing 0.5 M sodium phosphate, pH 7.2, 7% sodium dodecyl sulphate, 1% crystalline BSA, 1 mM EDTA, 40 m g/ml denatured salmon sperm DNA and about 1.times.106 cpm/ml of the PCR probe (supra). After hybridization for 12 h at 65° C., the filters were washed twice at room temperature in 2×SSC (30 mM sodium citrate, 0.3 M NaCl), 0.1% SDS and then at 65.degree. C. in 2×SSC, 0.1% SDS for 20 min and exposed to Kodak X-OMAT AR film. The filter replica B were hybridized with the labeled oligonucleotide noggin D in 6×SSC, 0.1% SDS at 51° C. for 12 h followed by wash at 2×SCC, 0.1% SDS at room temperature, and in 6×SSC, 0.1% SDS at 50° C. and exposed to Kodak X-OMAT AR film. Positive plaques from all replicas were isolated and purified by re-screening as above. Purified positive plaques were suspended in 500 μM (100 mM NaCl, 10 mM MgSO$_4$7H$_2$O, 50 mM Tris HCl pH 7.5, 0.01% gelatin). 160 μl of phage suspension was mixed with 0.5 ml saturated NM538 culture, incubated for 20 min at 37° C. and then inoculated into 250 ml LB containing 10 mM Mg SO$_4$, 0.2% maltose. The cultures were incubated until cell lysis (7-8 hr) at 37° C. The phage lysates were used for phage DNA purification by the Qiagen procedure according to the manufacturers recommendations (Qiagen).

Sequencing. Sequencing was performed by using the Applied Biosystems Model 373A automatic sequencer and Applied Biosystems Taq DyeDeoxym Terminator Cycle Sequencing Kit. Filters hybridized to the PCR mouse noggin probes (SEQ ID NOs:18 and 20) showed two strong signals corresponding to phage plaques named hnogλ-9 and hnogλ-10. These plaques also hybridized to degenerate oligonucleotide probe noggin D (SEQ ID NO:9) revealed that these clones correspond to the human noggin gene. In addition, two other plaques named hnogλ-5 and hnogλ-7 produced slightly weaker signals when hybridized to the PCR probes. These clones correspond to either human noggin or related gene(s). All of the human DNA inserts can be excised from the vectors using known restriction sites as described in the literature regarding each particular library.

A 1.6 kb Sac1 fragment from clone hnogλ-9 containing the human noggin gene was subcloned and the nucleotide sequence determined as set forth SEQ ID NO:1. The amino acid sequence for human noggin, as deduced from the nucleotide sequence, is also set forth in SEQ ID NO:2.

Example 2

Tissue Localization of Message for Human Noggin

Probes were prepared as set forth in Example 4 of U.S. Pat. No. 6,277,593 (SEQ ID NOs:3 and 4). A DNA fragment of approximately 300 bp was obtained by PCR amplification of a mouse cDNA clone prepared as described in Example 3 of U.S. Pat. No. 6,277,593.

RNA Preparation and Northern Blots. Selected tissues were dissected from Sprague-Dawley rats and immediately frozen in liquid nitrogen. RNAs were isolated by homogenization of tissues in. 3 M LiCl, 6 M urea, as described in Bothwell et al. (1990 Methods of Cloning and Analysis of Eukaryotic Genes, Boston. RNAs (10 µg) were fractionated by electrophoresis through quadruplicate 1% agarose-formaldehyde gels followed by capillary transfer to nylon membranes (MagnaGraph, Micron Separations Inc.) with 10×SSC (pH7). RNAs were UV-cross-linked to the membranes by exposure to ultraviolet light (Stratalinker, Stratagen, Inc.) and hybridized at 68° C. with radiolabled probes in the presence of 0.5 M $NaPO_4$ (pH 7), 1% bovine serum albumin (fraction V, Sigma, Inc.) 7% SDS, 1 mM EDTA (Mahoudi et al. (1989) Biotechniques 7:331-333), 100 µg/ml sonicated, denatured salmon sperm DNA. Filters were washed at 68° C. with 3×SSC, 0.1% SDS and subjected to autoradiography for 1 day to 2 weeks with one or two intensifying screens (Cronex, DuPont) and X-ray film (AR-5, Kodak) at 70° C. Ethidium bromide staining of the gels demonstrated that equivalent levels of total RNA were being assayed for the different samples (Maisonpierre et al. (1990) Science 247:1446-1451). RNA was prepared from a variety of human cell lines, as described in U.S. Pat. No. 6,277,593.

Example 3

Neural Induction by Noggin

Preparation of Xenous noggin CHO cell conditioned medium. Xenopus noggin CHO conditioned medium was made by selecting for stably transfected CHO cells. Dihydrofolate reductase (DHFR) deficient CHO parental cells (J. Papkoff, Syntex Research) were transfected with a Xenopus noggin expression plasmid containing noggin in tandem with the dihydrofolate reductase gene. Growth in nucleoside free medium was used to select for successfully transfected cells. Nine colonies of transfectants were picked and grown up individually. The noggin gene in these cells was amplified by slowly increasing the dose of methotrexate, an inhibitor of DHFR. The presence of noggin transcripts was first tested by Northern analysis. Subsequently, two clones, B3 and C3, were shown to secrete noggin protein, since conditioned medium from these lines was capable of dorsalizing ventral marginal zones. Furthermore, by labeling B3 cellular proteins with $^{35}S$-methionine, noggin protein could be identified as a band of about 30 kD on reducing SDS-PAGE, and a band of 60 kD on non-reducing SDS-PAGE indicating it forms the expected dimer. These properties matched those of the noggin protein previously produced in Xenopus oocytes supra, (Smith et al. (1993) Nature 361: 547-49). B3 conditioned medium was collected in a mixture of 1 part alpha MEM and 9 parts CHO—S-SFMII (Gibco-BRL). The cells were allowed to condition the medium for 3 days. Control medium from parental cells (CHO dhfr−) was collected identically. Twenty fold concentrated medium was made using Centriprep 10 concentrators, where the 20 fold change is measured by volume.

Purification of human noggin from COS cells. Human noggin protein was purified by a cationic exchange column. COS/M5 cells were transiently transfected with a human noggin expression plasmid, pCAE11. Cells were allowed to condition DMEM (Specialty Media) for two to three days, after which the medium was removed. Particulates from the medium were removed by a centrifugation step and subsequent passage through a 0.2 µm cellulose acetate filter. This cleared medium was pumped onto a MonoS (Pharmacia) column which was washed with several volumes 40 mM sodium phosphate (pH 7.3), 150 mM NaCl, 1 mM EDTA. Proteins were then eluted in a linear gradient with 40 mM sodium phosphate (pH 8.5), 1.8M NaCl, 1 mM EDTA. Noggin protein elutes at 0.8 M NaCl and is $\geq$90% pure by SDS-PAGE.

Xenopus otx Isolation. To isolate *Xenopus Otx* clones a tadpole head cDNA library (Hemmati-Brivaniou et al. (1989) Development 106:611-617) was screened with a mouse otx cDNA (S-L Ang and Rossant, Toronto) at low stringency. The clones that were picked fell into two classes. One class, which we have designated otxA, included pXOT21.2, the probe used here. By in situ hybridization, transcripts are first detected prior to gastrulation in the superficial layer on the dorsal side. During neurulation a large anterior domain expressed the gene, and includes both neural and non-neural tissues. After a decline in expression in the tailbud tadpole, the gene is reexpressed specifically in the brain and eyes.

Ventral Marginal Zone Assay. *Xenopus laevis* embryos are fertilized and de-jellied as described (Condie et al. (1987) supra), routinely the evening before dissections. Embryos are cultured overnight at 15° C. The vitelline membrane surrounding each developing embryo is manually removed the following morning at the late blastula stage. Until dissection, the embryos are maintained in ⅓.times. modified ringers in agarose coated dishes.

Ventral Marginal Zone Dissection. Embryos are oriented with their yolky vegetal hemisphere up so the dorsal side can be identified. The dorsal side of the early gastrula is marked by the presence of a small arc of dense pigment called the "dorsal lip" which marks the start of involution of dorsal mesoderm. The ventral marginal zone (VMZ) is found directly opposite the dorsal lip, and is dissected. Since the vitelline membrane has been removed, the embryo tends to flatten. Using a specially constructed knife made of an eyebrow, mounted onto a glass pipet with wax, two cuts are made through the flattened embryo from the top facing vegetal pole through to the animal pole. The cuts are made such that they isolate approximately 30-60 degrees of the ventral side away from more lateral tissues. A third cut which is perpendicular to the first two cuts completely isolates the ventral marginal zone tissue away from the rest of the embryo. This third cut is at the level of approximately two thirds of the radius of the embryo from the center. Prior to treatment the VMZ is washed 1.times. in the culture medium.

Approximately between 5 to 10 VMZs are used per assay. The washed VMZs are dropped gently (trying to minimize transfer of liquid) into eppendorf tubes containing the desired treatment protein medium for assay. The VMZs are allowed to develop to the late neurula or early tailbud stage as assessed by control whole embryo development. At this time RNA is isolated from the VMZs and control whole embryos as described (Condie et al. (1987) supra. The expression of muscle actin in VMZs indicates a dorsalization event (Lettice and Slack (1933) Development 117: 263-72). RNA from each sample is run on a formaldehydeagarose gel and blotted to gene screen. The blot is then hybridized with a Xenopus muscle actin probe (Dworkin-Rastl et al. (1986) J. Embryol. exp. Morph. 91:153-68). Quantitation of dorsalization can be carried out by normalizing muscle actin signal to that of the ubiquitously expressed EF-1α (Krieg et al. (1989) Devl. Biol. 133, 93-100). Quantitation is done using phosphor imaging.

RNase Protection Assay. RNase protection was carried out (Melton et al. (1984) Nucleic Acids Res. 12:7035-56), with the modification that digestion was carried out at room temperature (22° C.) using RNase Ti only (Calbiochem 556785) at 10 units/ml. 20-30 animal caps were harvested for each lane, of this 80% was used for neural markers and 10% for muscle actin and collagen type II. For goosecoid and brachyury 20 caps were used. Exposures ranged from 12 hours to 5 days. In all cases, films were preflashed. In cases where a marker was not expressed, the result was confirmed with greater sensitivity using phosphor imaging. Results are shown in U.S. Pat. No. 6,277,593, herein specifically incorporated by reference in its entirety.

Example 4

Production of Recombinant Human Noggin From E. coli and Baculovirus

Genetic Engineering and Cell Culture. A lactose inducible expression plasmid was constructed by replacing the Swa1/Bsm1 region of pRPN40 (Masiakowski et al. (1991) J. Neurochem. 57:1003-1012) with the Swa1/Bsm1 region of the human noggin gene obtained by PCR and spanned by the same restriction sites, resulting in plasmid pRG301. pRG301 is a high copy number kanamycin resistant plasmid derived from pBR322 with the human noggin gene under the control of the lacUV5 promoter. A plasmid containing the high copy number kanamycin resistant gene was deposited with the Agricultural Research Collection (NRRL), Peoria, Ill., and bears accession number B-18600. This plasmid was described in U.S. patent application Ser. No. 07/478,338, which is incorporated by reference herein in its entirety. E. coli W3110lacIq cells transformed with pRG301 were grown at 37° C., induced with lactose, harvested by centrifugation, washed once with 100 mM Tris-HCl, 50 mM EDTA pH 8 and stored frozen.

Recovery From Inclusion Bodies. E. coli cell paste (32 g) was suspended in ten volumes (v/w) of 50 mM Tris HCl-pH 8.0-5 mM EDTA, lysed in a French Press at 8,000 psi and 80° C. and centrifuged at 8,000×g for 30 min at 40° C. The pellet containing noggin was suspended in the original volume of 2 M urea-20 mM Tris HCl, pH 8.0 and stirred for 30 min. The suspension was centrifuged at 8,000×g at 40° C. for 30 min and the pellet consisting mostly of inclusion bodies (IB) was suspended in 20 volumes (v/w) of 6 M guanidine HCl, 50 mM Tris HCl, 1 mM EDTA, 50 mM DTT and stirred for one hour at room temperature. After centrifugation at 8,000×g for 30 min, the supernatant containing 0.45-0.50 g denatured and reduced noggin was diafiltered against 10 volumes of 6 M urea-50 mM sodium acetate pH 4.5-1 mM EDTA-0.1 mM DTT using Omega 10,000 MW cut-off membranes. The diafiltrate containing 0.4-0.44 g noggin was loaded at a flow rate of 30 ml/min onto a 2.6×10 cm column of S-Sepharose (Pharmacia), equilibrated in 6 M urea-50 mM sodium acetate-1 mM EDTA-0.1 mM DTT pH 4.5. The column was first washed with the same buffer and then with a one liter gradient (0-1M NaCl) at a flow rate of 30 ml/min. Fractions containing noggin were identified by gel electrophoresis and pooled. The yield was 0.2-0.25 g noggin.

Refolding. The denatured and reduced noggin solution was adjusted to 0.05-0.2 mg/ml protein concentration and brought to 1.5-2.5 M guanidineHCl-0.1 M Tris HCl pH 8.0-0.1 mM EDTA-0.2-2 mM reduced glutathione-0.02-0.2 mM oxidized glutathione (preferably at a ratio of 10:1 reduced to oxidized glutathione) at 40° C. under slow stirring. After 24-72 hours, two refolded noggin isoforms were identified by RP-HPLC chromatography. The refolded noggin solution was diafiltered against 20 volumes of 0.05 M sodium acetate pH 4.5, brought to 50 mM potassium phosphate pH 7.2 and stirred slowly at 40° C. for 1 hour minimum. Misfolded noggin precipitated and was removed by centrifugation for 30 min at 8,000×g.

Reverse Phase HPLC Chromatography. Refolded noggin can be purified by chromatography on a 12 mm C8, 1×25 cm Dynamax 300 A column equilibrated in solvent A (0.1% TFA in water). After loading, the column was washed with solvent A and was developed at a flow rate of 4 ml/min according to the following protocol: (a) 10 min isocratically at 70% of solvent A, 30% of solvent B (0.1% TFA in acetonitrile); 30 min linear gradient to 60% solvent B and 40% solvent A. Correctly refolded noggin elutes earlier at 44%-46% solvent B. The yield was 0.07-0.1 g noggin.

Production of Human Noggin in Baculovirus Cell Culture. The SF21 line of Spodoptera frugiperda was routinely maintained as cell monolayers in Grace's Insect Cell medium supplemented with lactalbumin hydrolysate and yeastolate (Gibco). This medium completed with 10% v/v heat-inactivated fetal calf serum (Irvine Scientific) is identified as TMNFH-10. Cells were also cultured in serum-free medium (SF-900-II; Gibco) after adaptation. Suspension cultures in either medium were raised in microcarrier culture flasks (Bellco) using a stirring speed of 80 rpm. All cultures were maintained at >96% viability, as judged by trypan blue exclusion.

Construction of Recombinant Baculovirus. Sequences corresponding to human noggin were excised as a 5'-BamH1-Pst1-3' fragment from an expression plasmid containing the human noggin gene. This fragment was inserted into BamH1-Pst1 digested pVL1393 (Invitrogen). The resulting plasmid, pTR 1009, has the human noggin sequence immediately downstream of the polyhedrin promoter of Autrographa californica Multiple Nuclear Polyhedrosis Virus (AcMNPV), and this promoter-heterologous gene fusion is flanked in turn by recombination targets derived from the AcMNPV polyhedrin region. Recombinant plasmid DNA was purified by alkaline lysis and CsCl centrifugation. SF21 cells were co-transfected with plasmid and viral DNA by the following method: Plasmid DNA (3 mg) was mixed with 0.5 mg linearized, deleted viral DNA (Baculo Gold.TM., Pharminigen), and precipitated with ethanol. Dried DNA was then resuspended in water (50 ml), mixed with 1.5 ml Grace's medium, and 30 ml Lipofectin-.upsilon. cationic liposomes (BRL). The DNA-liposome-mixture was vortexed, allowed to stand at room temperature for 15 minutes and added dropwise to a monolayer of SF21 cells ($2\times10^6$ cells/60 mmplate). After incubation at 27° C. for four hours, 2 ml TMNFH-10 was added and the culture returned to incubation for 5 days. Tissue culture medium was harvested and used as a source of virus for plaque isolation.

Recombinant virus was isolated by multiple rounds of plaque purification on SF21 cells. Diluted virus (0.5 ml) was adsorbed to cell monolayers ($2\times10^6$ cells/60 mmplate) for a period of one hour at 27° C., aspirated, and virus plaques were allowed to develop with an overlay of 0.5% agarose in TMNFH-10 medium for a period of 6 days. Virus plaques were picked after microscopic inspection, and eluted into 2 ml SF900-II medium. Virus stocks were amplified by low multiplicity (0.1 pfu/cell) infection. Virus clones expressing noggin were identified by metabolic labeling of infected cultures with $^{35}$S-methionine and $^{35}$S-cysteine and analyzing total labeled protein by polyacrylamide gel electrophoresis and autoradiography. A labeled protein of the expected apparent Mr of 20,000-30,000 was detected by this method in candidate clones but not in control cultures.

Expression and Purification of Baculovirus-derived Noggin. SF21 cells were cultured in suspension flasks to a density of approximately 1.8.times.106/ml in SF900-II medium. Cultures (500 ml) were collected by centrifugation at 1000.times.g for 10 min and resuspended in 20 ml of growth medium containing 5-10 pfu/cell recombinant virus. Virus was allowed to adsorb for 1 hour at room temperature with gentle mixing. Infected cells were then diluted to their original volume with fresh growth medium, and incubated at 270° C. for 3 days. Cells and debris were subsequently clarified from the growth medium by centrifugation at 1000.times.g for 20 min.

Cell supernatants were brought to pH 8.0, passed through a 0.45 mm Millipak 60 filter and applied to a Fast S column that had been equilibrated in 25 mM HEPES pH 8.0. The column was washed with the same buffer and developed with a linear NaCl gradient to remove other medium components. Noggin eluted from this column at 1 M NaCl. Results are shown in U.S. Pat. No. 6,277,593, herein specifically incorporated by reference in its entirety.

Example 5

Construction of Noggin Mutein and Pharmacokinetic Properties

Construction of hNOGΔB2 from hNOG. To engineer the noggin mutein hNOGΔB2, the heparin-binding region of human noggin (hNOG) (SEQ ID NO:2) encoded by amino acids 133 to 144 was deleted, resulting a protein having the sequence of SEQ ID NO:10. The sequence of hNOGΔB2 was verified by DNA sequence analysis. Recombinant hNOG and hNOGΔB2 were expressed in *E. coli*, refolded and purified to homogeneity as described in Valenzuela et al. (1995) J. Neuroscience 15(9):6077-6084).

Pharmacokinetic profiling of hNOG and hNOGΔB2 by ELISA. BALB/c mice were injected with 250 μg of hNOG (intraperitoneally or intravenously) or hNOGΔB2 (intraperitoneally). Approximately 200 μl of blood was collected using heparin-free needles prior to injection and at 2, 6, and 24 hours post-injection. Serum was recovered by standard methods. The level of noggin protein present in the sera was determined by ELISA.

A two-site ELISA was developed using two rat-derived anti-human noggin monoclonal antibodies. Antibody RP57-16, which binds an epitope located within the N-terminal half of noggin, was coated onto Immulon-4 plates (Nunc) in PBS at a concentration of 2 μg/ml. Unbound antibody that had not bound was removed, and the plates were treated with 10 mg/ml BSA solution in PBS for 2 hours to block any free protein-binding sites. The test sera were initially diluted 20-fold, added to the plates, and 2-fold serial dilutions were performed in PBS. Purified hNOG or hNOGΔB2 in mouse serum was used as a standard and subjected to the same serial dilution as the test sera. Following binding to RP57-16 for 1 hour, the plates were washed 3 times with PBS, and then 1 μg/ml solution of the anti-noggin biotinylated monoclonal RP57-21-biotin, which binds an epitope located within the C-terminal half of noggin, was added to each well. After 1 hour of incubation, the plates were washed three times with PBS. To detect RP57-21-biotin, the plates were incubated with a Streptavidin-Alkaline Phosphatase conjugate (Sigma) at a 1:5000 dilution, for 1 hour. The plates were washed with Tris buffered saline plus 0.05% Tween-20 (Sigma), and bound streptavidin-alkaline phosphatase conjugate was detected colorimetrically as described above. The amount of noggin in each sample was determined by comparing the signal for each sample against its standard curve and the half-lives were determined.

Example 6

Animal Model of Human FOS Disease rhBMP4- or rhBMP2-Induced Heterotopic Ossification. An in vivo model of endochondral osteogenesis, which closely resembles the histopathology of an FOP lesion, was developed using a percutaneous delivery of a basement membrane protein (Matrigel™, Becton Dickinson, Bedford, Mass.) impregnated with recombinant human BMP4 (rhBMP4, Regeneron Pharmaceuticals) or with recombinant human BMP2 (rhBMP2, Regeneron Pharmaceuticals). Matrigel is liquid at 4° C., allowing the addition of the rhBMP4. Upon subcutaneous injection, the bolus of rhBMP4-impregnated matrigel solidifies at 37° C. to form a localized source of BMP. rhBMP4 or rhBMP2 implants (12.5 μg/250 μl rhBMP) were injected subcutaneously into the abdominal musculature of C57BL/6 mice (experiments using rhBMP4) or BALB/c mice (experiments using rhBMP2) and recovered at time points from eight hours to three weeks for histological and immunohistochemical analysis. All mice were obtained from Jackson Labs.

Local delivery of hNOG in a rhBMP2 implant. To assess the ability of unmodified noggin to block BMP-mediated bone formation, BALB/c male mice (4 mice per treatment group) were implanted subcutaneously with matrigel containing: (a) vehicle alone; (b) 15 μg of rhBMP2; or (c) 15 μg of rhBMP2 plus 26.3 μg of hNOG (equimolar amounts of rhBMP2 and hNOG). The matrigel implants were assayed after 14 days, fixed in formalin, sectioned, and stained with hemoxylin/eosin for examination using light microscopy. Histological evaluation of the sections was performed in a blinded manner, where the investigator evaluating the sections was not informed of the treatment regimen.

Construction of recombinant adenovirus H5.01CMVhNOGΔB2 and H5.010CMVLacZ. The E1-deleted recombinant adenoviruses H5.010CMVhNOGΔB2 and H5.00CMVLacZ used in this study carried a minigene cassette expressing either the engineered human noggin gene (hNOGΔB2) or the β-galactosidase gene (LacZ) under the control of the cytomegalovirus (CMV) early promoter. The vector was constructed by homologous recombination in HEK293 cells co-transfected with ClaI-restricted sub360 viral DNA and the shuttle plasmid pAdCMVhNOGΔB2 or pAdCMVLacZ. After two rounds of plaque purification, the vector was propagated in HEK293 cells and purified by two rounds of CsCl density-gradient centrifugation.

In Vivo Somatic Cell Gene Transfer of hNOGΔB2. With IACUC approval, animals were injected via tail veins with either $1 \times 10^{10}$, $3 \times 10^{10}$ or $1 \times 10^{11}$ viral particles/mouse of recombinant adenovirus encoding hNOGΔB2 (H5.010CMVhNOGΔB2) or a control adenovirus encoding LacZ (H5.010CMVLacZ). hNOGΔB2 levels in peripheral blood/serum were monitored on day 1, 4, 11 and 18 of the study using the two-site ELISA for noggin.

Four days following viral gene transfer, the abdominal musculature of C57BL/6 mice was injected on one side of the midline with 250 μl of carrier alone, and on the contralateral side with 250 μl of carrier combined with recombinant human BMP4 at a final concentration of 50 mg/ml. Implants were recovered at 7 and 14 days after injection. Standard techniques were used to evaluate the histologic stages of bone formation and to identify specific cell types present in the tissue.

Deposit of Microorganisms: The following were deposited with the American Type Culture Collection, 12301 Parklawn Drive, Rockville, Md. 20852 under the terms of the Budapest Treaty: phage hnogλ-5 ATCC 75311 deposited 9-23-92; phage hnogλ-7 ATCC 75309 deposited 9-23-92; phage hnogλ-9 ATCC 75310 deposited 9-23-92; phage hnogλ-10 ATCC 75308 deposited 9-23-92; hybridoma RP57-16 ATCC CRL 11446 deposited 8-25-93.

We claim:

1. A method of treating a bone morphogenetic protein (BMP)-related disorder or condition, comprising administering a BMP antagonist to a subject suffering from BMP-induced osteogenesis characterized by heterotopic ossification, wherein the BMP-induced osteogenesis is treated, wherein the BMP antagonist is human noggin (hNOG) (SEQ ID NO:2) for local administration, or hNOGΔB2 (SEQ ID NO:10) for systemic or local administration.

2. The method of claim 1, wherein the BMP-related disorder or condition is heterotopic cranial synostosis, fibrodysplasia ossificans progressiva (FOP), or sclerostosis.

3. A method of inhibiting the progress of a bone morphogenetic protein (BMP)-related disorder or condition, comprising administering human noggin (hNOG) (SEQ ID NO:2) for local administration or hNOGΔB2 (SEQ ID NO:10) for local or systemic administration to a subject suffering from BMP-induced osteogenesis characterized by heterotopic ossification, wherein the BMP-induced osteogenesis is treated.

4. The method of claim 3, wherein the BMP-related disorder or condition is heterotropic cranial synostosis or fibrodysplasia ossificans progressiva (FOP).

* * * * *